United States Patent [19]
Parker et al.

[11] Patent Number: 5,389,074
[45] Date of Patent: Feb. 14, 1995

[54] BODY INSERTION TUBE WITH ANESTHETIC JACKET

[75] Inventors: James N. Parker; Brian S. Pazevic, both of San Diego, Calif.

[73] Assignee: The Regents of the University of California, Oakland, Calif.

[21] Appl. No.: 143,872

[22] Filed: Oct. 27, 1993

[51] Int. Cl.[6] .................. A61M 29/00; A61M 31/00; A61M 16/00
[52] U.S. Cl. .................. 604/96; 128/207.15; 604/54; 604/280
[58] Field of Search .............. 128/207.14, 207.15; 604/27, 28, 35, 43, 54, 96–103, 266, 268, 280, 119

[56] References Cited

U.S. PATENT DOCUMENTS

| | | | |
|---|---|---|---|
| 2,854,982 | 10/1958 | Pagano | 604/101 |
| 3,173,418 | 3/1965 | Baran | 128/207.15 |
| 3,394,705 | 7/1968 | Abramson | 604/280 |
| 3,593,713 | 7/1971 | Bogoff | 604/96 |
| 3,670,729 | 6/1972 | Bennett et al. | 128/214.4 |
| 3,981,299 | 9/1976 | Murray | 604/43 |
| 4,211,233 | 7/1980 | Lin | 604/96 |
| 4,417,576 | 11/1983 | Baran | 128/207.15 |
| 4,423,725 | 1/1984 | Baran et al. | 128/207.15 |
| 4,536,180 | 8/1985 | Johnson | 604/119 |
| 4,693,243 | 9/1987 | Buras | 128/207.15 |
| 4,717,379 | 1/1988 | Ekholmer | 604/280 |
| 4,927,418 | 5/1990 | Dake et al. | 604/264 |
| 4,977,894 | 12/1990 | Davies | 128/207.15 |
| 4,994,033 | 2/1991 | Shockey et al. | 604/101 |
| 5,004,455 | 4/1991 | Greenwood et al. | 604/280 |
| 5,021,044 | 6/1991 | Sharkawy | 604/280 |
| 5,049,132 | 9/1991 | Shaffer et al. | 604/101 |
| 5,146,916 | 9/1992 | Catalani | 604/43 |
| 5,213,576 | 5/1993 | Abiuso et al. | 604/96 |
| 5,313,939 | 5/1994 | Gonzalez | 604/28 |

Primary Examiner—C. Fred Rosenbaum
Assistant Examiner—Frank Wilkens, III
Attorney, Agent, or Firm—John L. Rogitz

[57] ABSTRACT

A body insertion tube can be configured as a nasogastric (NG) tube or endotracheal (ET) tube. When the tube is an NG tube, the tube has a distal segment positionable in the esophagus and a stomach segment connected to the distal segment and positionable in the stomach for aspirating fluids therefrom. An inflatable perforated jacket is positioned around a substantial portion of the distal segment such that anesthetic can be directed into the jacket and out of the perforations to anesthetize substantially all of the nasal passages and throat during intubation. When the tube is an ET tube, the tube has a distal segment positionable in the trachea, and an inflatable cuff is positioned around the distal segment of the tube. An inflatable perforated jacket surrounds a substantial segment of the tube such that anesthetic can be directed through the jacket to anesthetize substantially all of the throat and vocal cords during intubation.

24 Claims, 3 Drawing Sheets

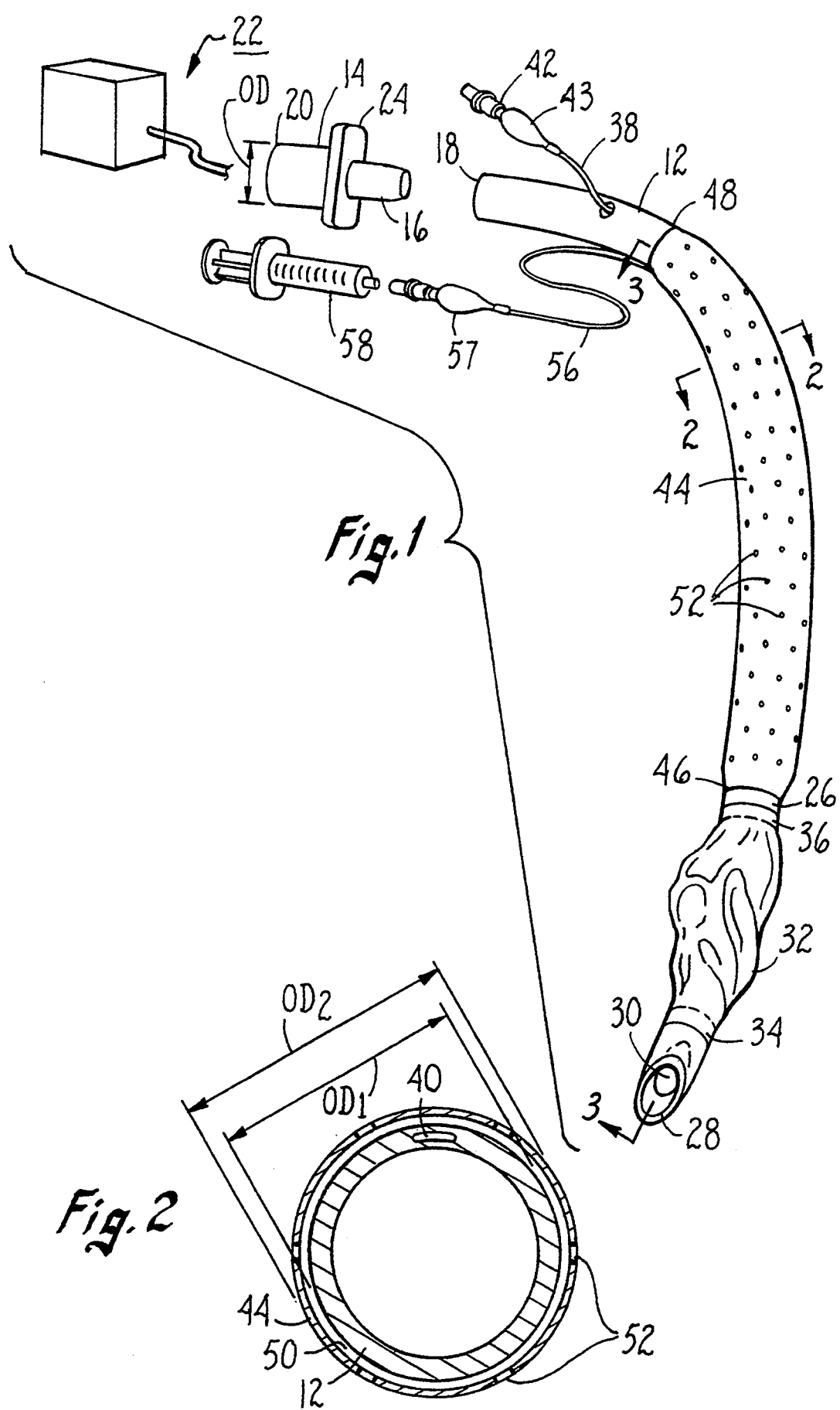

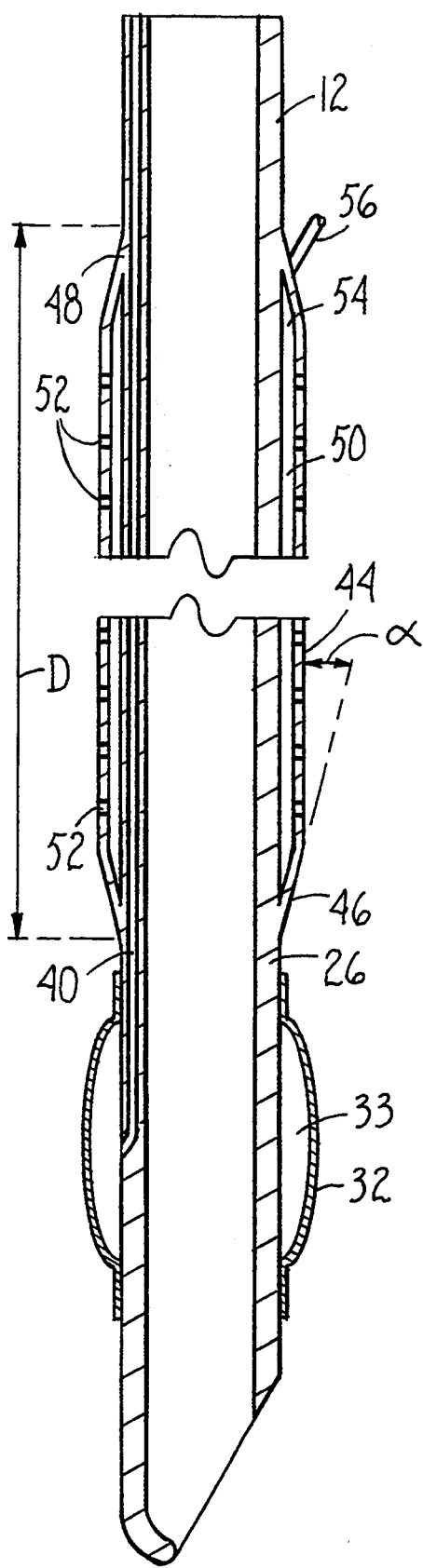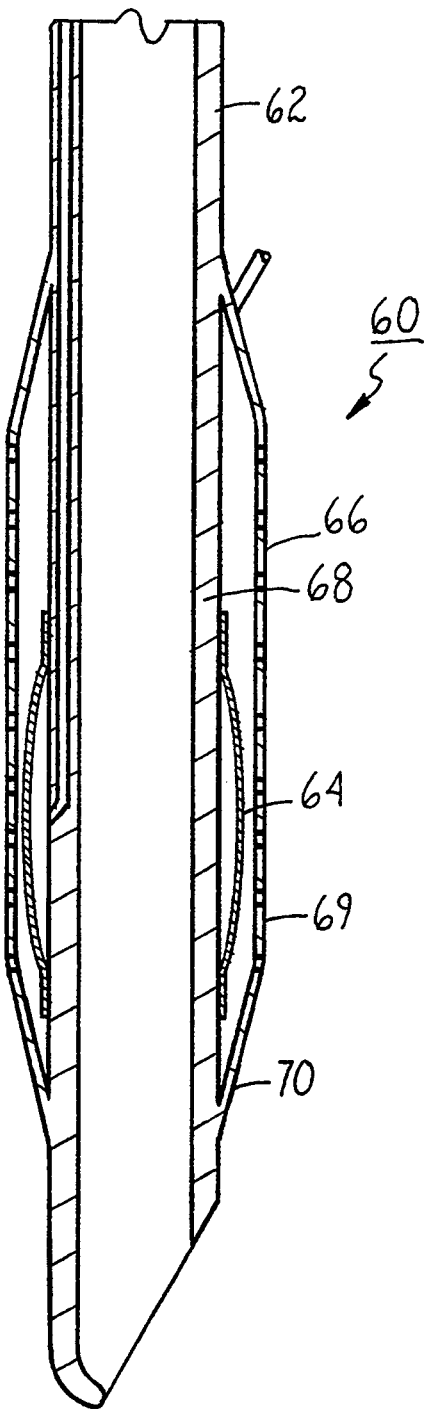

BODY INSERTION TUBE WITH ANESTHETIC JACKET

FIELD OF THE INVENTION

The present invention relates generally to body insertion tubes, and more particularly to methods and apparatus for maintaining nasogastric tubes and endotracheal tubes with a minimum of patient discomfort.

BACKGROUND

The use of body insertion tubes, i.e., catheters that can be advanced (intubated) into a human body passage, is well-known. Of particular concern to the present invention are body insertion tubes which are configured either as endotracheal (ET) tubes or nasogastric (NG) tubes. ET tubes are catheter-like devices which are advanced through the mouth into a patient's pharynx and trachea to establish a pathway for ventilation to and from the lungs. NG tubes, on the other hand, are catheter-like devices which are advanced through the nose, pharynx, and esophagus to establish a pathway for fluid communication to and from the stomach, usually to aspirate stomach fluids.

In either case, areas of the body in opposition to the tube (e.g., the vocal cords, nasal passages, and epiglottis) are sensitive and can be irritated by the body insertion tube. Indeed, it can be appreciated that intubation can cause significant patient discomfort. Not only is the discomfort unpleasant for the patient, but it can induce involuntary reactions, such as muscle spasms, retching, etc., on the part of the patient. These involuntary reactions can understandably hinder ET tube or NG tube therapy and endanger the life of the patient.

Not surprisingly, devices have been introduced for anesthetizing portions of a body passage to reduce patient discomfort arising from catheter intubation. For example, U.S. Pat. No. 5,146,916 to Catalani discloses an ET tube that has a well-known inflatable cuff for establishing a fluid seal between the trachea and ET tube such that respiration can occur only through the ET tube. The Catalani invention includes a perforated cannula which extends along one side of the tube and which terminates in a perforated diffuser that surrounds the cuff, and anesthetic can be directed through the perforations to anesthetize portions of the trachea. Catalani also discloses an embodiment which has a small perforated diffuser cuff surrounding the ET tube proximal to the cuff.

Unfortunately, none of the Catalani devices as disclosed will, under all circumstances, completely anesthetize the more sensitive portions of the body passage into which the ET tube is positioned, namely the vocal cords and epiglottis which are ordinarily proximal to a properly placed cuff. More particularly, the perforated cannula of Catalani will not direct anesthetic onto the entire vocal cord/epiglottis region of a patient, but only onto the portion of the vocal cord/epiglottis region that directly faces the perforated cannula. Also, the small proximal diffuser cuff of Catalani is too narrow to ensure complete anesthetization of the vocal cord/epiglottis region, particularly given the positioning uncertainties inherent in ET tube use. In other words, the user of the Catalani device can unintentionally position the small diffuser cuff above or below the vocal cords, and thereby fail to ensure that anesthetic is directed onto the vocal cords.

In contrast to the Catalani device, U.S. Pat. No. 3,593,713 to Bogoff discloses a urethra catheter that has a tube with inflatable cuff for holding the tube within the urethra, and the Bogoff device includes a perforated jacket which encircles the tube. Anesthetic can be directed through the perforations to anesthetize portions of the urethra which are proximal to the cuff.

Unfortunately, the Bogoff device, like all urethra catheters, is unsuitable for ET and NG applications. Urethra catheters must be made of relatively pliant material, to avoid undue patient discomfort (particularly in males) when the device is in place. The pliancy of such catheters, however, would make them extremely difficult if not impossible to properly advance through a person's pharynx into the trachea or esophagus, particularly without the aid of a rigid positioning stylet, which may induce patient trauma, particularly when the catheter is advanced blindly as most NG tubes ordinarily are. This problem is particularly acute in NG applications, wherein the NG tube must be advanced through a person's nose, thereby obviating use of a styler altogether. Thus, urethra catheters do not have sufficient axial rigidity to permit them to be advanced into a patient's body passage through the pharynx. Also, urethra catheters are too short for NG tube applications.

Further, as recognized by the present invention, the pliant material from which urethra catheters must be made would tend to collapse when the lumen of the catheter is evacuated (e.g., in NG tube applications), or to unduly expand when the lumen is pressurized (e.g., in ET tube applications). Undue expansion of the lumen in ET tube applications is most undesirable, because the volume of oxygen actually provided to the patient (and not simply to expanding the ET tube) consequently cannot be reliably established. Collapse of the lumen in NG tube applications would prevent effective stomach suctioning.

Accordingly, the present invention recognizes the need to provide a body insertion tube which includes means for anesthetizing substantially all of the body passage in which the tube is intubated, which has axial rigidity sufficient to permit the tube to be advanced into a patient's body passage through the pharynx, and which will not collapse or expand under ET or NG application conditions.

It is accordingly an object of the present invention to provide a body insertion tube that has means for anesthetizing the body passage into which the tube is intubated. Another object of the present invention is to provide a body insertion tube which can easily be advanced into a body passage. Still another object of the present invention is to provide a body insertion tube which is easy to use, and cost-effective to manufacture.

SUMMARY OF THE INVENTION

A device is disclosed which is engageable with a source of anesthetic fluid, and the device can be advanced into a patient for establishing a pathway for fluid communication through the patient's pharynx while reducing patient discomfort. In accordance with the present invention, the device includes an elongated flexible tube that has a distal segment positionable in a body passage that is in communication with the pharynx. The tube also has a proximal segment, and the tube has sufficient axial rigidity to permit it to be advanced into the body passage. A jacket surroundingly engages the distal segment of the tube along a substantial length of the distal segment. Importantly, the jacket is formed with a plurality of perforations along its entire length and circumference, and anesthetic fluid from the source can be directed out of the perforations of the jacket onto the body passage of the patient to anesthetize a substantial portion of the body passage.

In a presently preferred embodiment, the jacket has distal and proximal end portions, with each end portion being attached to the tube. To facilitate easily advancing the distal segment of the tube with jacket in the body passage of the patient, the end portions are faired into the surface of the tube.

In one intended embodiment, the body passage is the trachea, the tube is an endotracheal (ET) tube, and the device further includes an inflatable cuff positioned around a portion of the distal segment of the tube distal to the jacket to establish a fluid seal between the trachea and the ET tube. In the ET tube embodiment, the jacket can include a cuff extension which surrounds the cuff. Alternatively, the jacket can include a distal extension located distal of the cuff, a proximal section located proximal to the cuff, and a connecting lumen extending therebetween for establishing a passageway for anesthetic communication from the proximal section of the jacket to the distal section of the jacket.

Preferably, the ET tube defines a lumen and includes a hollow connector which is engageable with a respiratory support system. The tube is made of a plastic material, preferably polyvinyl chloride (PVC), which is sufficiently strong to prevent expansion of the lumen when oxygen is directed from the support system through the lumen into the patient's lungs.

The jacket has a distal end positioned on the tube adjacent the cuff and a proximal end. To ensure that substantially all of the vocal cords and epiglottis regions are anesthetized, the distance between the ends of the jacket is between approximately five centimeters and fifteen centimeters (5–15 cm), and preferably about seven centimeters (7 cm).

In addition to the ET tube embodiment, the tube of the present invention can be configured as a nasogastric (NG) tube, and the body passage includes the nasopharynx, pharynx, and esophagus. In such an embodiment, the NG tube includes a stomach segment extending distally away from the distal segment, and the stomach segment is formed with a plurality of axially-spaced openings through which stomach fluid can be aspirated. Further, the NG tube is made of a plastic material sufficiently strong to prevent collapse of the lumen when stomach fluids are aspirated through the tube.

A hollow connector is provided that has a proximal end engageable with an NG support system tube and a distal end engageable with the NG tube. The connector has a midpoint, and is radially tapered inwardly from the midpoint to each end to facilitate engaging the NG tube and support system tube. Preferably, the NG tube includes a main lumen in communication with the openings of the stomach segment and a vacuum break lumen in communication with the openings.

In another aspect of the present invention, an endotracheal (ET) tube assembly includes an ET tube which has a distal segment that is sufficiently axially rigid to permit the distal segment to be advanced through a patient's mouth into the patient's trachea. An inflatable cuff is positioned around the distal segment of the ET tube to establish a fluid seal between the trachea and the ET tube. Also, a jacket is surroundingly engaged with the distal segment of the ET tube. In accordance with the present invention, the jacket has a plurality of perforations along its entire length and circumference, and the jacket has a distal end positioned on the ET tube adjacent the cuff and a proximal end. To ensure that substantially all of the vocal cords and epiglottis regions are anesthetized, the distance between the ends of the jacket is between approximately five centimeters and fifteen centimeters (5–15 cm).

In another aspect of the present invention, a nasogastric (NG) tube assembly includes an NG tube which has a stomach segment that is sufficiently axially rigid to permit the stomach segment to be advanced through a patient's nasal passage into a patient's esophagus. The stomach segment is formed with a plurality of axially-spaced openings through which stomach fluid can be aspirated. Furthermore, a jacket is surroundingly engaged with the NG tube proximal to the axially-spaced openings, and the jacket has a plurality of perforations along its entire length and circumference. Consequently, anesthetic can be directed through the perforations against substantially all of the patient's nasal passages, pharynx, and proximal portion of the esophagus in which the assembly is intubated.

In still another aspect of the present invention, a method is disclosed for establishing a pathway for fluid communication from a patient's throat to a body passage of the patient in communication with the throat, while minimizing patient discomfort. The method of the present invention includes the steps of providing a body insertion tube which is sufficiently rigid to permit the tube to be advanced into the body passage. A segment of the tube is surrounded with a perforated anesthetic jacket, and the jacket has a proximal end and a distal end axially spaced from the proximal end a distance of at least five centimeters (5 cm). Consequently, when the tube is properly positioned, anesthetic fluid can be directed through the perforations against substantially all of the patient's throat tissue which is adjacent the tube. The tube is accordingly advanced into the body passage, and anesthetic fluid is directed through the perforations of the jacket to anesthetize the throat.

The details of the present invention, both as to its construction and operation, can best be understood in reference to the accompanying drawings, in which like numerals refer to like parts, and which:

BRIEF DESCRIPTION OF THE DRAWINGS

FIG. 1 is an exploded perspective view of the body insertion tube of the present invention configured as an endotracheal (ET) tube, with a respiratory support system shown schematically;

FIG. 2 is a cross-sectional view of the body insertion tube, as seen along the line 2—2 in FIG. 1;

FIG. 3 is a cross-sectional view of the body insertion tube with the cuff inflated, as would be seen along the line 3—3 in FIG. 1;

FIG. 4 is cross-sectional view of an alternate embodiment of the body insertion tube, as would be seen along the line 3—3 in FIG. 1, wherein the anesthetic jacket covers the cuff;

DETAILED DESCRIPTION OF THE PREFERRED EMBODIMENT

Figure 5:
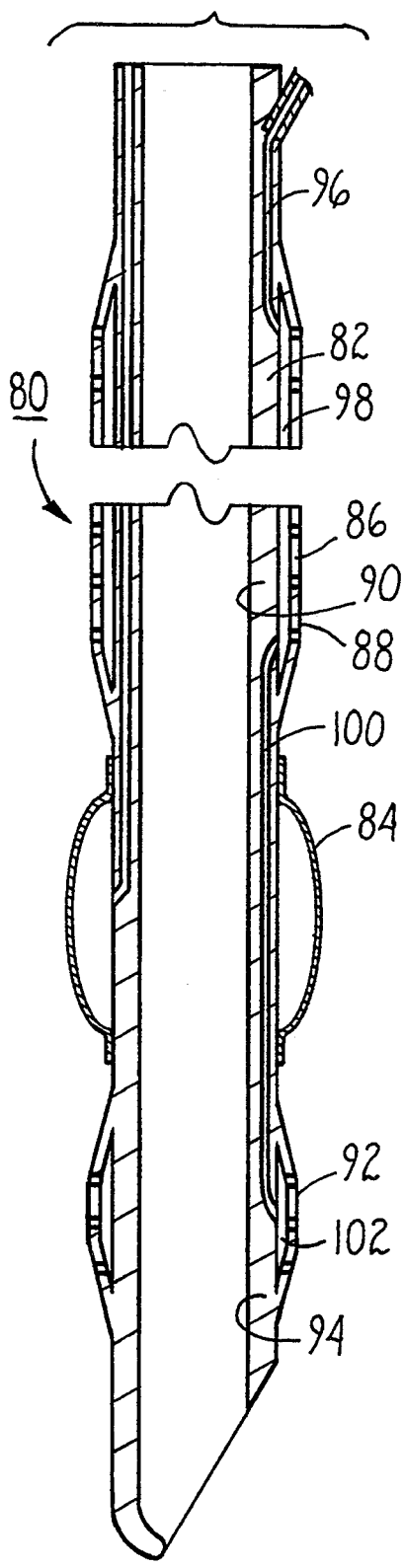
FIG. 5 is cross-sectional view of another alternate embodiment of the body insertion tube, as would be seen along the line 3—3 in FIG. 1, wherein the anesthetic jacket includes a section proximal to the cuff and a section distal to the cuff.

Referring initially to FIG. 1, a body insertion tube is shown, generally designated 10. As can be appreciated in reference to FIG. 1, in one presently preferred embodiment the body insertion tube 10 can be configured as an endotracheal (ET) tube apparatus that has an elongated hollow flexible ET tube 12 made of suitable transparent plastic material, such as polyvinyl chloride (PVC), that is biocompatible. Also, the ET tube 12 is preferably made from a material which, when configured as shown, possesses axial rigidity sufficient for permitting the ET tube 12 to be manually advanced through a patient's mouth, pharynx, and into the trachea. Accordingly, when made of PVC, the ET tube 12 has a wall thickness "t" of between about six-tenths of a millimeter and three and one-half millimeters (0.6 mm–3.5 mm). If desired, the ET tube 12 can be materially biased into the slightly arcuate shape shown, to facilitate positioning the ET tube 12 in the trachea of a patient.

FIG. 1 shows that a hollow rigid plastic connector 14 has a cylindrical distal segment 16 which can be engaged with a proximal end 18 of the ET tube 12 in an interference fit therewith. Also, the ET connector 14 has a cylindrical proximal segment 20, and the proximal segment 20 can be engaged with a respiratory support system 22. Preferably, the ET tube 12 is made of a material, e.g., relatively stiff PVC, which possesses sufficient strength to prevent unwanted swelling of the ET tube 12 when oxygen from the system 22 is directed through the ET tube 12 to the bronchi.

Preferably, the proximal segment 20 of the ET connector 14 has an outside diameter "OD" of fifteen millimeters (15 mm). A generally parallellepiped-shaped flange 24 is formed on the ET connector 14 between the distal and proximal segments 16, 20.

FIG. 1 further shows that the ET tube 12 has a distal segment 26 configured for positioning within a patient's trachea, to respirate oxygen to and carbon dioxide from the patient through the two bronchial passages. Accordingly, the distal segment 26 of the ET tube 12 terminates in an open distal end 28, and the distal end 28 is bevelled as shown relative to the long axis of the ET tube 12. Also, an opening 30 is formed in the ET tube 12 generally opposite the bevelled open distal end 28.

An inflatable cuff 32 is positioned around a portion of the distal segment 26 of the ET tube 12 to establish a chamber 33 (FIG. 3) between the cuff 32 and the ET tube 12. The cuff 32 is made of a plastic material, and is bonded to the ET tube 12 at its distal and proximal ends 34, 36. To provide a path for fluid into and out of the cuff 32 for respectively inflating and deflating the cuff 32, a cuff inflation line 38 is in fluid communication with a cuff lumen 40 (best shown in FIG. 2) that is formed in the wall of the ET tube 12, and the cuff lumen 40 in turn communicates with the chamber 33. The cuff inflation line 38 is attached to a fluid fitting 42. The fitting 42 can include a valve 43 configured as is common in the ET tube art for selectively permitting fluid flow through the cuff inflation line 38. A source of fluid (not shown) is engageable with the fitting 42 for infusing fluid into the chamber 33 to thereby inflate the cuff 32. As the skilled artisan will recognize, the inflated cuff 32 establishes a fluid seal between the trachea and the ET tube 12, such that respiration occurs solely through the ET tube 12. Also, the cuff 32, when inflated, prevents gastric fluids from the stomach from entering the esophagus.

The present invention contemplates that the ET tube 12 with cuff 32 as described above may advantageously be a standard ET assembly, such as the ET assemblies made by Malinckrodt, Inc. or Sheridan Catheter Corp.

In cross-reference to FIGS. 1, 2, and 3, the body insertion tube 10 includes a jacket 44 which surrounds the ET tube 12 and is preferably co-extruded therewith during manufacturing. Alternatively, the jacket 44 can be manufactured separately from the ET tube 12, and then bonded to the ET tube 12 after manufacture of the ET tube 12.

FIG. 3 best shows that the jacket 44 has a distal end 46 which is attached to or formed integrally with the ET tube 12 just proximally to the cuff 32. Also, the jacket 44 has a proximal end 48 which is attached to or formed integrally with the ET tube 12, and an anesthetic chamber 50 is formed between the jacket 44 and ET tube 12. The length of the jacket 44, i.e., the distance "D" between the distal and proximal ends 46, 48 when the ET tube 12 is straight, is between about five centimeters and fifteen centimeters (5 cm–15 cm), and is preferably about seven centimeters (7 cm).

To facilitate easily advancing the body insertion tube 10, the ends 46, 48 of the jacket 44 are faired into the ET tube 12, as best shown in FIG. 3. Stated differently, the distal and proximal ends 46, 48 of the jacket 44 are tapered relative to the long axis of the ET tube 12, i.e., the ends 46, 48 establish an obtuse angle $\alpha$ with respect to the long axis of the ET tube 12.

FIGS. 2 and 3 also show that the jacket 44 is formed throughout its length and circumference with a plurality of perforations 52 which communicate with the anesthetic chamber 50. In a presently preferred embodiment, the perforations 52 are formed by repeatedly piercing the jacket 44 with a twenty five (25) to thirty (30) gauge needle (not shown). Alternatively, the perforations 52 can be formed in the jacket 44 during the manufacturing of the jacket 44.

Preferably, the jacket 44 is relatively thin-walled, and the anesthetic chamber 50 occupies a comparatively small volume, to minimize the radial profile of the tube 10 for facilitating easy positioning. In the embodiment shown in FIG. 2, the ET tube 12 has an outside diameter "$OD_1$", the jacket 44 has an outside diameter "$OD_2$", and the difference between "$OD_1$" and "$OD_2$" is about one-half millimeter (0.5 mm).

FIG. 3 shows that an anesthetic lumen 54 is formed in the ET tube 12 in communication with the anesthetic chamber 50. An anesthetic line 56 (FIG. 1) is in turn in communication with the anesthetic lumen 54, and a syringe 58 or other source of anesthetic fluid can be engaged with the anesthetic line 56 to infuse anesthetic through the anesthetic line 56, anesthetic lumen 54, and into the anesthetic chamber 50. From the anesthetic chamber 50, the anesthetic is directed through the perforations 52 and onto tissue which surrounds the jacket 44. A fitting 57 which is in all essential respects identical to the fitting 42 can be provided for engaging the syringe 58 with the anesthetic line 56.

Accordingly, the skilled artisan will appreciate that with the combination of structure disclosed above, the distal segment 26 of the body insertion tube 10 can be positioned into a patient's trachea, and the vocal cords and epiglottis areas which surround the tube 10 can be substantially completely anesthetized by infusing anesthetic from the syringe 58 and out of the perforations 52. Furthermore, the relatively long length "D" of the jacket 44 ensures that anesthetic will be directed against the sensitive vocal cords and epiglottis, despite variations in the positioning of the distal segment 26 of the ET tube 12 in the trachea of the patient. Moreover, by circumscribing the jacket 44 around the ET tube 12, and perforating the jacket 44 throughout its surface area, anesthetic is delivered to tissue along the length of the jacket 44 in a 360° pattern.

Now referring to FIG. 4, an alternate embodiment of the body insertion tube of the present invention is shown, generally designated 60. As shown, the tube 60 includes an ET tube 62 with cuff 64 and perforated anesthetic jacket 66. The jacket 66 surrounds a distal segment 68 of the ET tube 62, and a cuff extension 69 of the jacket 66 extends around the cuff 64. A distal end 70 of the cuff extension 69 of the jacket 66 is bonded to the ET tube 62 distal to the cuff 64. In such an embodiment, the jacket 66 is made of the same flaccid material as the cuff 64, so as not to unduly impede inflation of the cuff 64. When it is desired to anesthetize the tissue surrounding the cuff 64, the cuff 64 is deflated, anesthetic is directed through the perforations of the jacket 66, and then the cuff 64 reinflated. The tube 60 is in all other essential respects identical in construction to the tube 10 shown in FIGS. 1-3.

FIG. 5 shows yet another embodiment of the body insertion tube of the present invention, generally designated 80. As shown, the tube 80 includes an ET tube 82 with cuff 84 and perforated anesthetic jacket 86. The jacket 86 includes a circumferentially perforated proximal section 88 which surrounds a first segment 90 of the ET tube 82 proximal to the cuff 84. Additionally, the jacket 86 includes a circumferentially perforated distal section 92 which surrounds a second segment 94 of the ET tube 82 distal to the cuff 84.

An anesthetic lumen 96 is formed in the ET tube 82, and the anesthetic lumen 96 communicates with a first anesthetic chamber 98 located between the proximal section 88 of the jacket 86 and the ET tube 82. Also, a connecting lumen 100 is formed in the ET tube 82, and the connecting lumen 100 communicates with the first anesthetic chamber 98. Further, as shown in FIG. 5, the connecting lumen 100 communicates with a second anesthetic chamber 102 which is located between the distal section 92 of the jacket 86 and the ET tube 82.

Accordingly, anesthetic fluid can be infused through the anesthetic lumen 96, first anesthetic chamber 98, and out of the proximal section 88 of the jacket 86 to anesthetize tissue which surrounds the first segment 90 of the ET tube 82. Further, the anesthetic fluid can communicate with the second anesthetic chamber 102 through the connecting lumen 100, for directing the anesthetic out of the distal section 92 of the jacket 86 to anesthetize tissue which surrounds the second segment 94 of the ET tube 82.

Figure 6:
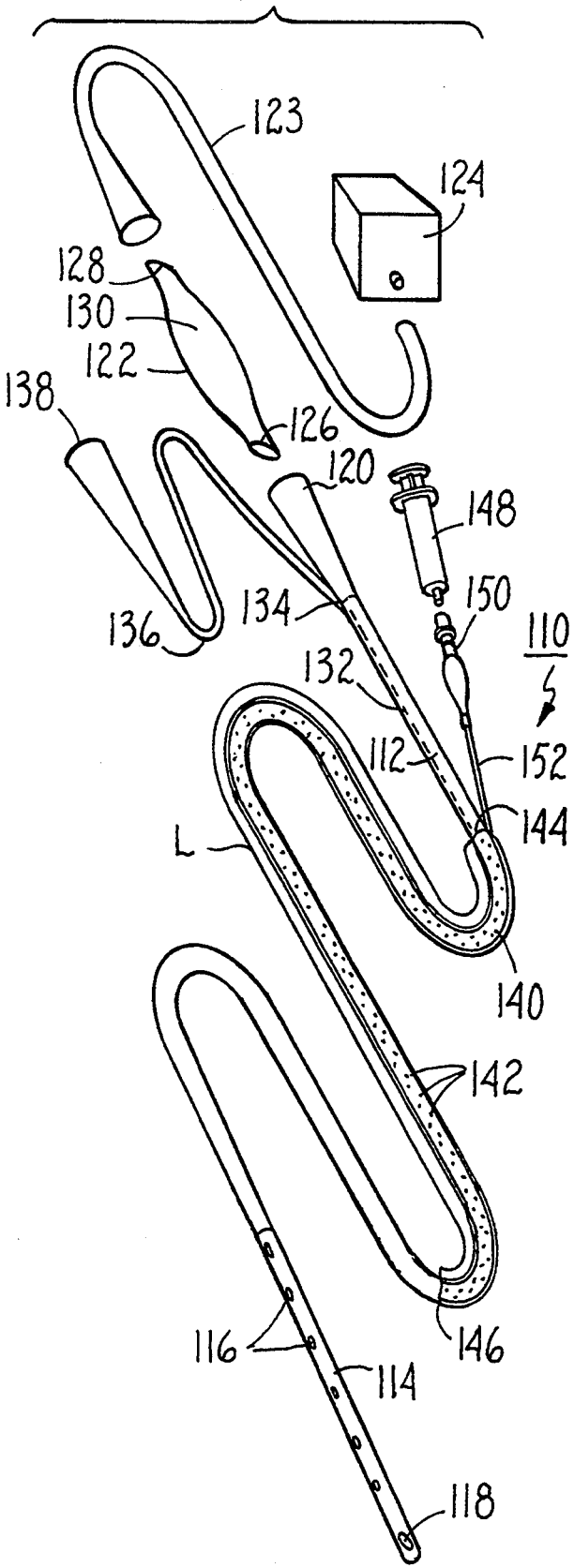
FIG. 6 is a perspective view of still another alternate embodiment of the body insertion tube of the present invention, configured as a nasogastric (NG) tube, with an NG support system shown schematically.

Now referring to FIG. 6, an embodiment of the body insertion tube of the present invention which is configured for nasogastric (NG) applications is shown, generally designated 110. As shown, the tube 110 includes a flexible NG tube 112 that has a distally-located stomach segment 114, and a plurality of axially-spaced openings 116 are formed in the stomach segment 114.

Preferably, the NG tube 112 is made from a material (e.g., relatively stiff PVC) which, when configured as shown, possesses axial rigidity sufficient for permitting the NG tube 112 to be manually advanced through a patient's nose, pharynx, and into the esophagus and stomach.

FIG. 6 shows that the NG tube 112 includes a main lumen 118 which communicates with the openings 116. The main lumen 118 has a proximal end 120, and a rigid hollow plastic connector 122 can be engaged with the proximal end 120 of the main lumen 118 and the connector tube 123 of an ancillary support system 124. As is known in the art, the support system 124 can be used, e.g., for aspirating the contents of a stomach of a patient (not shown). The NG tube 112 is made of a material, e.g., PVC, which is sufficiently strong to ensure that the main lumen 118 does not collapse when aspirating fluids from a patient's stomach.

Preferably, the connector 122 has first and second ends 126, 128 and a midpoint 130 therebetween. As shown, the ends 126, 128 of the connector 122 are bevelled relative to the long axis of the connector 122. Also, the connector 122 is radially tapered inwardly from the midpoint 130 to each end 126, 128 to facilitate engaging the NG tube 112 with the tube 123 of the support system 124.

A vacuum break lumen 132 (shown in phantom in FIG. 6) is also formed in the NG tube 112, side-by-side with the main lumen 118. Like the main lumen 118, the vacuum break lumen 132 communicates with the openings 116 which are formed in the stomach segment 114. Also, the vacuum break lumen 132 has a proximal end 134, and a hollow flexible so-called "pigtail" tube 136 is in communication with the proximal end 134 of the vacuum break lumen 132.

The pigtail tube 136 has an outwardly-flared proximal end 138 for receiving the connector 122 to connect the main lumen 118 with the vacuum break lumen 132 during periods when stomach aspiration is to be halted. Otherwise, during periods when the stomach is to be aspirated, the connector 122 is engaged with the support system 124 to connect the system 124 with the main lumen 118. It will be appreciated by the skilled artisan that in such a configuration, air can pass through the vacuum break lumen 132 into the main lumen 118 near the distal end of the NG tube 112 to break excessive vacuum in the main lumen 118 which could be caused by unintended plugging of the openings 116.

The NG tube 112 described above can be a standard eighteen (18) french NG tube such as the Salem Sump ® NG tube made by Sherwood Medical of St. Louis, Mo.

FIG. 6 shows that a circumferentially-perforated jacket 140 having perforations 142 has a proximal end 144 and a distal end 146, and the ends 144, 146 of the jacket 140 are attached to or formed integrally with the NG tube 112. Like the ends 46, 48 of the jacket 44 shown in FIGS. 1-3, the ends 144, 146 of the jacket 140 shown in FIG. 6 are faired into the corresponding tube, i.e., the NG tube 112, to facilitate smooth intubation. The perforations 142 can be formed in the jacket 140 during manufacturing of the jacket 140, or formed afterwards by repeatedly piercing the jacket 140 with a twenty five (25) or thirty (30) gauge needle.

The jacket 140 may be made of flaccid or non-flaccid plastic material. Preferably, the jacket 140 is coextruded with the NG tube 112 during the manufacturing process. Alternatively, the ends 144, 146 of the jacket 140 may be bonded, e.g., with silicon glue, to the NG tube 112. In either case, the jacket 140 preferably adds only about one-half millimeter (0.5 mm) or less to the radial cross-sectional profile presented by the NG tube 112, to facilitate easily advancing the NG tube 112 into a patient.

It can appreciated in reference to FIG. 6 that the jacket 140 is relatively long, to ensure that the entire nasopharynx, pharynx, and proximal third of the esophagus which are adjacent the catheter 110 are anesthetized. In other words, the length "L" between the ends 144, 146 of the jacket 140 (along the length of the portion of the NG tube 112 that is covered by the jacket 140) is sufficient so that when the tube 110 is properly positioned in the patient, anesthetic is directed against substantially all of the areas of tissue adjacent the tube 110, from the tip of the patient's nose to the proximal third of the esophagus. As recognized by the present invention, by so directing anesthetic, the most sensitive portions of the body passage in which the tube 110 is intubated are anesthetized. In one presently preferred embodiment, the length "L" is between about thirty centimeters and seventy five centimeters (30 cm–75 cm).

Once the NG tube 112 is properly positioned in a patient, anesthetic from a syringe 148 can be infused through a connector 150 and infusion line 152 into the space that is established between the jacket 140 and NG tube 112. The anesthetic then flows out of the perforations 142 to anesthetize the nasopharynx, pharynx, and proximal portion of the esophagus.

While the particular body insertion tube with anesthetic jacket as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. A device engageable with a source of anesthetic fluid, the device being advanceable into a patient for establishing a pathway for fluid communication through the patient's pharynx while reducing patient discomfort, comprising:
    a source of pressure;
    an elongated flexible tube defining a lumen in fluid communication with the source of pressure, the tube having a distal segment positionable in a body passage of the patient that is distal to the pharynx, the tube being made of plastic such that the tube has sufficient strength to substantially prevent deformation of the tube when the source of pressure is activated; and
    a jacket surroundingly engaged with the distal segment of the tube along at least five centimeters (5 cm) of the distal segment, the jacket being formed with a plurality of perforations along its entire length and circumference, wherein anesthetic fluid from the source of anesthetic fluid can be directed out of the perforations of the jacket onto the body passage of the patient to anesthetize a substantial portion of the body passage.

2. The device of claim 1, wherein the jacket has distal and proximal end portions each attached to the tube, and the end portions are faired into the surface of the tube to facilitate easily advancing the distal segment of the tube with jacket in the body passage of the patient.

3. The device of claim 1, wherein the body passage is the trachea, the tube is an endotracheal (ET) tube, and the device further comprises an inflatable cuff positioned around a portion of the distal segment of the tube distal to the jacket.

4. The device of claim 3, wherein the jacket includes a cuff extension surrounding the cuff.

5. The device of claim 3, wherein the jacket comprises a distal extension located distal of the cuff, a proximal section located proximal to the cuff, and a connecting lumen extending therebetween for establishing a passageway for anesthetic communication from the proximal section of the jacket to the distal section of the jacket.

6. The device of claim 3, wherein the tube defines a lumen, the source of pressure is a respiratory support system, the tube includes a hollow connector engageable with the respiratory support system, and wherein the tube is made of a plastic material sufficiently strong to prevent expansion of the lumen when oxygen is directed from the support system through the lumen into the patient's lungs.

7. The device of claim 6, wherein the jacket has a distal end positioned on the tube adjacent the cuff and a proximal end, and the distance between the ends of the jacket is between approximately five centimeters and fifteen centimeters (5–15 cm).

8. The device of claim 7, wherein the distance between the ends of the jacket is approximately seven centimeters (7 cm).

9. The device of claim 1, wherein the body passage includes the nasopharynx, pharynx, and esophagus and the tube is a nasogastric (NG) tube, and the NG tube includes a stomach segment extending distally away from the distal segment, wherein the stomach segment is formed with a plurality of axially-spaced openings for aspirating stomach fluid therethrough, and the tube is made of a plastic material sufficiently strong to prevent collapse of the lumen when stomach fluids are aspirated therethrough.

10. The device of claim 9, further comprising a hollow connector having a proximal end engageable with an NG support system tube, a distal end engageable with the NG tube, and a midpoint therebetween, wherein the connector is radially tapered inwardly from the midpoint to each end to facilitate engaging the NG tube and support system tube.

11. The device of claim 10, wherein the NG tube includes a main lumen in communication with the openings of the stomach segment and a vacuum break lumen in communication with the openings.

12. An endotracheal (ET) tube assembly, comprising:
    a source of respiratory oxygen;
    an ET tube defining a lumen in fluid communication with the source of oxygen and having a distal segment;
    an inflatable cuff positioned around the distal segment of the ET tube for establishing a fluid seal between the tube and the trachea when the cuff is inflated with fluid; and
    a jacket surroundingly engaged with the distal segment of the ET tube and having a plurality of perforations along its entire length and circumference, wherein the jacket has a distal end positioned on the tube adjacent the cuff and a proximal end, wherein the distance between the ends of the jacket is between five centimeters and fifteen centimeters (5-15 cm), the distal segment of the ET tube being positionable in a patient's pharynx to establish a pathway for fluid communication between the source of oxygen and the patient's lungs, and wherein the ET tube is made of material sufficiently strong to prevent swelling of the ET tube when oxygen from the source is directed through the lumen to the patient's lungs.

13. The ET tube assembly of claim 12, further comprising a source of anesthetic liquid in fluid communication with the jacket for anesthetizing a substantial portion of the body passage.

14. The assembly of claim 13, wherein the jacket has distal and proximal end portions each attached to the tube, and the end portions are faired into the surface of the tube to facilitate easily advancing the tube with jacket in the body passage of the patient.

15. The assembly of claim 14, wherein the jacket includes a cuff extension surrounding the cuff.

16. The assembly of claim 14, wherein the jacket comprises a distal extension located distal of the cuff, a proximal section located proximal to the cuff, and a connector tube extending therebetween for establishing a passageway for anesthetic communication from the proximal section of the jacket to the distal section of the jacket.

17. The assembly of claim 14, wherein the tube defines a lumen and includes a hollow connector engageable with a respiratory support system, and wherein the tube is made of a plastic material sufficiently strong to prevent expansion of the lumen when oxygen is directed from the support system through the lumen into the patient's lungs.

18. A nasogastric (NG) tube assembly, comprising:
a source of vacuum for aspirating fluid from a patient's stomach;
an NG tube having a stomach segment formed with a plurality of axially-spaced openings for aspirating stomach fluid therethrough and a proximal segment defining a lumen in fluid communication with the source of vacuum; and
a jacket surroundingly engaged with the NG tube proximal to the axially-spaced openings and having a plurality of perforations along its entire length and circumference through which anesthetic can be directed against substantially all of the patient's nasal passages, pharynx, and proximal portion of the esophagus in which the assembly is intubated, wherein
the tube is made of a plastic material sufficiently strong to prevent collapse of the lumen when the source of vacuum is activated to aspirate stomach fluid.

19. The assembly of claim 18, further comprising:
a source of anesthetic liquid in fluid communication with the jacket.

20. The assembly of claim 19, wherein the jacket has distal and proximal end portions each attached to the NG tube, and the end portions are faired into the surface of the tube to facilitate easily advancing the distal segment of the tube with jacket in a body passage of the patient.

21. The assembly of claim 20, further comprising a hollow connector having a proximal end engageable with an NG support system tube, a distal end engageable with the tube, and a midpoint therebetween, wherein the connector is radially tapered inwardly from the midpoint to each end to facilitate engaging the tube and support system tube.

22. The device of claim 21, wherein the tube includes a main lumen in communication with the openings of the stomach segment and a vacuum break lumen in communication with the openings.

23. A method for establishing a pathway for fluid communication from a patient's throat to a body passage of the patient in communication with the throat, while minimizing patient discomfort, comprising the steps of:
(a) providing a body insertion tube made of plastic and defining a lumen, the body insertion tube being sufficiently strong to substantially prevent deformation of the body insertion tube when the body insertion tube is pressurized or evacuated;
(b) surrounding a segment of the tube with a perforated anesthetic jacket, the jacket having a proximal end and a distal end axially spaced from the proximal end a distance of at least five centimeters (5 cm), such that when the tube is properly positioned, anesthetic fluid can be directed through the perforations against substantially all of the patient's throat tissue which is adjacent the tube;
(c) advancing the tube into the body passage;
(d) engaging the tube with a source of pressure such that the lumen of the tube is in fluid communication with the source; and
(e) directing anesthetic fluid through the perforations of the jacket to anesthetize the throat.

24. A device advanceable into a patient for establishing a pathway for fluid communication through the patient's pharynx while reducing patient discomfort, comprising:
a source of anesthetic fluid;
a source of pressure;
an elongated flexible tube defining a lumen and having a distal segment positionable in a body passage of the patient that is distal to the pharynx and a proximal segment configured for establishing fluid communication between the source of pressure and the lumen of the tube, the tube having sufficient strength to substantially prevent deformation of the tube when the source of pressure is activated; and
a jacket surroundingly engaged with the distal segment of the tube along at least five centimeters (5 cm) of the length of the distal segment, the jacket being formed with a plurality of perforations along its entire length and circumference, wherein anesthetic fluid from the source can be directed out of the perforations of the jacket onto the body passage of the patient to anesthetize a substantial portion of the body passage.

* * * * *